(12) United States Patent
Klimant

(10) Patent No.: US 7,067,320 B2
(45) Date of Patent: Jun. 27, 2006

(54) SENSOR FOR LUMINESCENSE-OPTICAL DETERMINATION OF AN ANALYTE

(75) Inventor: Ingo Klimant, Mintraching (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 10/465,935

(22) PCT Filed: Dec. 21, 2001

(86) PCT No.: PCT/EP01/15186

§ 371 (c)(1),
(2), (4) Date: Apr. 19, 2004

(87) PCT Pub. No.: WO02/054076

PCT Pub. Date: Jul. 11, 2002

(65) Prior Publication Data
US 2004/0166024 A1    Aug. 26, 2004

(30) Foreign Application Priority Data
Dec. 29, 2000  (AT)  .................. A 2161/2000

(51) Int. Cl.
G01N 21/64  (2006.01)

(52) U.S. Cl. .................. 436/74; 436/79; 436/133; 436/113; 436/172; 436/163; 422/82.08

(58) Field of Classification Search .. 422/82.06–82.08, 422/82.11; 436/74, 79, 113, 133, 163, 172, 436/169, 170; 250/458.1, 459.1
See application file for complete search history.

(56) References Cited

U.S. PATENT DOCUMENTS

| | | | |
|---|---|---|---|
| 4,396,579 A | 8/1983 | Schroeder et al. | |
| 4,557,900 A | 12/1985 | Heitzmann | 422/55 |
| 4,822,746 A * | 4/1989 | Walt | 436/528 |
| 4,868,103 A | 9/1989 | Stavrianopoulos et al. | 435/5 |
| 4,929,561 A * | 5/1990 | Hirschfeld | 436/116 |
| 5,037,615 A * | 8/1991 | Kane | 422/82.08 |
| 5,114,676 A | 5/1992 | Leiner et al. | 422/82.06 |
| 5,194,393 A | 3/1993 | Hugl et al. | 436/525 |
| 5,254,477 A * | 10/1993 | Walt | 436/172 |
| 5,711,915 A | 1/1998 | Siegmund et al. | 422/68.1 |
| 5,942,189 A | 8/1999 | Wolfbeis et al. | 422/82.08 |
| 6,348,322 B1 | 2/2002 | Strittmatter | 435/7.8 |
| 6,613,282 B1 | 9/2003 | Huber et al. | |
| 6,835,351 B1 | 12/2004 | Huber et al. | |
| 2004/0175836 A1* | 9/2004 | Klimant | 436/164 |

FOREIGN PATENT DOCUMENTS

| | | |
|---|---|---|
| GB | 2 132 348 A | 7/1984 |
| JP | 59-170748 | 9/1984 |
| WO | WO 98/00714 | 1/1998 |
| WO | WO 00/42438 | 7/2000 |
| WO | WO 02/39083 A2 | 5/2002 |

* cited by examiner

Primary Examiner—Jeffrey R. Snay

(57) ABSTRACT

The invention relates to an optochemical sensor functioning in accordance with the FRET-principle and exhibiting an acceptor (chromophore or luminophore) responsive to an analyte contained in a sample medium as well as a donor (luminophore), characterized in that acceptor and donor are located in separate chemical phases, whereby the phase containing the donor is essentially impermeable to the sample medium or to components of the sample medium affecting the luminescence characteristics of the luminophore. The invention further relates to a method for qualitative and/or quantitative determination of at least one analyte and/or component of a gaseous or liquid measuring medium according to the FRET-principle, characterized by the use of the sensor according to the invention.

28 Claims, 6 Drawing Sheets

SENSOR FOR LUMINESCENSE-OPTICAL DETERMINATION OF AN ANALYTE

BACKGROUND OF THE INVENTION

The invention relates to a luminescence-optical method for qualitative and quantitative determination of at least one analyte and/or component of a liquid measuring medium containing a chromophore (or a luminophore) which is directly or indirectly responsive to the component to be determined by changing its absorption spectrum, and a luminophore which is not responsive to the component to be determined, where there is at least partial overlap between the emission spectrum of the luminophore and the absorption spectrum of the chromophore, and where the nonradiative energy transfer between luminophore and chromophore produces a measurable change in at least one luminescence characteristic of the luminophore. That principle is known as the so-called FRET-principle.

The invention further relates to an optochemical sensor for quantitative determination of at least one analyte and/or component of a gaseous or liquid measuring medium containing a chromophore (or a luminophore) which is directly or indirectly responsive to the component to be determined by changing its absorption spectrum, and a luminophore which is not responsive to the component to be determined, where there is at least partial overlap between the emission spectrum of the luminophore and the absorption spectrum of the chromophore, and where the nonradiative energy transfer between luminophore and chromophore produces a measurable change in at least one luminescence characteristic of the luminophore.

In the following, luminophores are understood as dyes which emit phosphorescence or fluorescence radiation upon suitable excitation. The absorption spectrum of the chromophore is influenced either directly by the component to be measured or indirectly by a chemical reaction product of the component to be measured. The term "quantitative determination of a chemical component" refers to the determination of concentration and activity as well as gas partial pressure, the values of at least one luminescence characteristic of the luminophore being used to infer the measured quantity.

A method and a sensor in which pH- and cation-sensitive chromophores (acceptor) are attached, preferably covalently, to a luminophore (donor) are known from U.S. Pat. No. 5,232,858. The pH-value and/or concentration of the cation to be determined in the measuring medium is derived from the luminescence decay time of the luminophore.

As far as the state of the art is concerned, U.S. Pat. No. 5,648,269 is also to be mentioned. This document suggests the application of the apparent luminescence decay time of the luminophore for determining the measured quantity. With luminophores with one decay time component, the apparent luminescence decay time is identical with the effective decay time. With luminophores with several decay time components, it is easier to evaluate the apparent decay time, however—in particular with systems that are not robust—there is the drawback of increasing errors.

Luminescence decay times may be obtained by means of phase-modulation or time-resolved luminescence measuring techniques, respectively.

A similar method is known from EP-A-0 214 768. Therein, the concentration of the parameter to be determined in the measuring medium is inferred from the luminescence intensity measured.

The rate of nonradiative energy transfer from donor to acceptor molecules depends on the spatial proximity of the molecules of the two substances. The transfer rate $k_T(r)$ is extremely responsive to the spatial distance r between donor and acceptor and decays with the sixth power of the distance $$k_T(r) = \frac{1}{\tau_D}\left(\frac{R_o}{r}\right)^6$$

whereby $\tau_D$ indicates the luminescence decay time of the donor in absence of the acceptor and $R_O$ indicates the characteristic Förster distance. The latter is that donor-acceptor distance in which a 50% efficiency of the energy transfer is provided. Depending on the respective donor-acceptor pair, $R_O$ is between 2 and 9 nm.

Due to the nonradiative energy transfer from donor to acceptor molecules, the macroscopically determinable values of the luminescence-optical parameters (luminescence quantum efficiency, luminescence intensity, luminescence decay time) of the luminophore will undergo a particularly efficient change if a substantial number of molecules of the two substances are brought into close spatial contact with each other.

To obtain close spatial contact, U.S. Pat. No. 5,232,858 proposes a covalent bonding of donor and acceptor molecules. In EP-A-0 214 768 individual donor and acceptor molecules are covalently attached to the surface of a joint substrate, such as glass.

The covalent bonding of donor and acceptor molecules as described in U.S. Pat. No. 5,232,858 has the advantage that the mean spatial distance of donor/acceptor may be kept as constant as possible. However, it is a disadvantage that particularly great synthesis efforts are required to produce covalent bonds between desirable luminophores and suitable pH- or ion-sensitive chromophores.

Considerable efforts are also needed to covalently attach donor and acceptor molecules to the surface of a joint substrate (EP-A-0 214 768), which, above all, brings about the drawback that boundary surface phenomena impair the quality of the measured results.

Thus, in U.S. Pat. No. 5,942,189 and U.S. Pat. No. 6,046,055 it is suggested that the luminophore and the chromphore are ionic substances of differing electrical charges, which are present as ionic pairs in a matrix material that is permeable to the chemical component to be determined.

The use of long-lived luminophores (having luminescence decay times >100 ns, preferably >1 µs), such as exhibited, for example, by metal-ligand complexes, certain porphyrins and lanthanides, is of utmost importance to a general commercial application. Long-lived luminescence provided, the opto-electronic arrangements and components for the determination of the luminescance decay time and/or values to be derived therefrom (for example, mean luminescance decay time, phase angle) may be determined in a particularly inexpensive manner by means of phase- or time-resolved methods.

However, the inventor of the present application has recognized that the above-mentioned, previously known methods bring about the mutual disadvantage that in particular the luminescence of long-lived luminophores is influenced by a number of components of the measuring medium. A known characteristic of such luminophores is the particularly great dependency of the luminescence characteristic on the $O_2$ content of the sample. Consequently, such luminophores are thus often used for determining the $O_2$ content (EP-A-0 907 074). When using those luminophores as donor dyes with sensors based upon the FRET-principle, it is thus necessary to exactly know or determine the $O_2$ content of the measuring medium and to carry out appropriate adjustments. Examples of further substances having an influence on the luminescence quantum efficiency are amines and water. In the course of continuous measurements (monitoring), luminescence dyes may be completely or partially destroyed by the emerging singlet-$O_2$. Accordingly, additives for limiting that process were suggested. However, a general drawback of known, advantageous luminescence dyes is the luminescence characteristics' sensitivity to minor changes of the chemical-physical microenvironment, caused by any components of the sample, in particular water. In case of sample media of unknown and/or variable chemical or biochemical compositions, that leads to a significant limitation of the measuring accuracy. For example, in medical diagnostics, reproducibilities of +/−5 milli-pH are expected in the field of blood-pH determination.

It is the object of the invention to improve luminescence-optical determination methods based upon the FRET-principle, which are based upon a luminophore (donor) and a chromphore (acceptor, indicator) reversibly binding the substance (analyte) to be determined or its reaction products, with regard to the susceptance to failure caused by components of the sample to be measured. Furthermore, particularly great chemical synthesis steps needed to obtain the spatial proximity of a substantial number of acceptor molecules and shielded donor molecules are to be avoided.

SUMMARY OF THE INVENTION

According to the invention, this object is achieved in that the luminophore (donor) and the chromophore (acceptor) are located in different chemical phases. The matrix material of the donor phase is to be essentially impermeable to components of the sample medium affecting the luminescence characteristics of the donor. The matrix material of the acceptor phase is to be permeable to the analyte or its reaction products, respectively.

Thus, the invention relates to an optochemical sensor functioning in accordance with the FRET-principle and containing a chromophore as well as a luminophore responsive to an analyte contained in a sample medium and is characterized in that the luminophore and the chromophore are located in separate chemical phases, whereby the phase containing the luminophore is impermeable to the sample medium or to components of the sample medium affecting the luminescence characteristics of the luminophore.

It is provided in a variant of the sensor according to the invention that the matrix material of the acceptor and donor phases is provided in mixed form or in the form of a thin layer (sensor layer), which may be attached to a transparent substrate or to a light guide. To decouple the sensor layer from possible disturbing optical interactions with the substance to be analyzed, an optical insulation layer permeable to the analyte and located between the sensor layer and the substance to be analyzed is optionally provided.

In a further embodiment (FIG. 5), the sensor layer consists of a thin porous material. The pores of that material contain the matrix material of the donor phase and the matrix material of the acceptor phase.

In a further embodiment (FIG. 6), the sensor layer is composed of a thin film representing the matrix material of the acceptor phase. Thereby, the matrix material of the donor phase is provided in homogeneously distributed fashion in the form of particles in the matrix material of the acceptor phase. The acceptor phase contains the acceptor molecules being homogeneously distributed and provided in a sufficient concentration so that an adequate number of acceptor molecules are located in the spatial proximity to the donor molecules provided in the donor phase which is necessary for the nonradiative energy transfer.

In a further embodiment (FIG. 7), the acceptor molecules are bound to the surface of the particles. Thereby, the chromophore may be bound at the surface adsoptively or electrostatically or, most preferably, covalently to functional groups. The bonding of the chromophore to the particle surface above all has the advantage that a) less chromphores are necessary, b) optical filter effects caused by excessive chromophore concentrations of the acceptor phase may be avoided, and c) the ratio of donor and acceptor molecules also determining the rate of energy transfer may be adjusted already on the level of producing the particles, thus being independent of the concentration of the acceptor molecules in the acceptor phase.

The method according to the invention serves for the qualitative and/or quantitative determination of at least one analyte and/or component of a gaseous or liquid measuring medium in accordance with the FRET-principle and is characterized by the use of a sensor according to the invention.

Preferably, the method according to the invention serves for the determination of the pH-value of a sample, for the determination of concentrations and/or activities of ions in a sample or for the determination of components exhibiting acid or alkaline reactions in an aqueous medium while being gaseous under normal conditions.

In particular, the method according to the invention serves for the determination of concentrations and/or activities of $Li^+$, $Na^+$, $K^+$, $Mg^{++}$, $Ca^{++}$ or $Cl^-$.

Furthermore, the method according to the invention preferably serves for the determination of $CO_2$ or $NH_3$ in a liquid measuring medium.

Further areas of application of the method according to the invention concern so-called transducers. Therein, the chromophore does not directly react with the analyte, but indirectly. Examples of that are so-called enzymatical sensors (for example, for determining urea and creatinine). Thereby, one or more enzymes react with the analyte, leading to the formation of a product which reacts directly with the chromophore.

Preferably, the measuring medium is a body fluid, in particular blood, plasma or serum.

Most advantageous luminophores (donor) used according to the invention are those which feature high luminescence quantum efficiency and long luminescence decay time (>100 ns). Preferred luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

Preferred pH- and cation-sensitive chromophores (acceptor) are anionic substances whose light absorption will change upon direct or indirect chemical/physical interaction with the component of the sample medium to be determined, and whose absorption spectrum overlaps the emission spectrum of the luminophore, at least partially.

BRIEF DESCRIPTION OF THE DRAWINGS

The invention will be explained in greater detail with reference to FIGS. 1–7.

DETAILED DESCRIPTION

Figure 1:
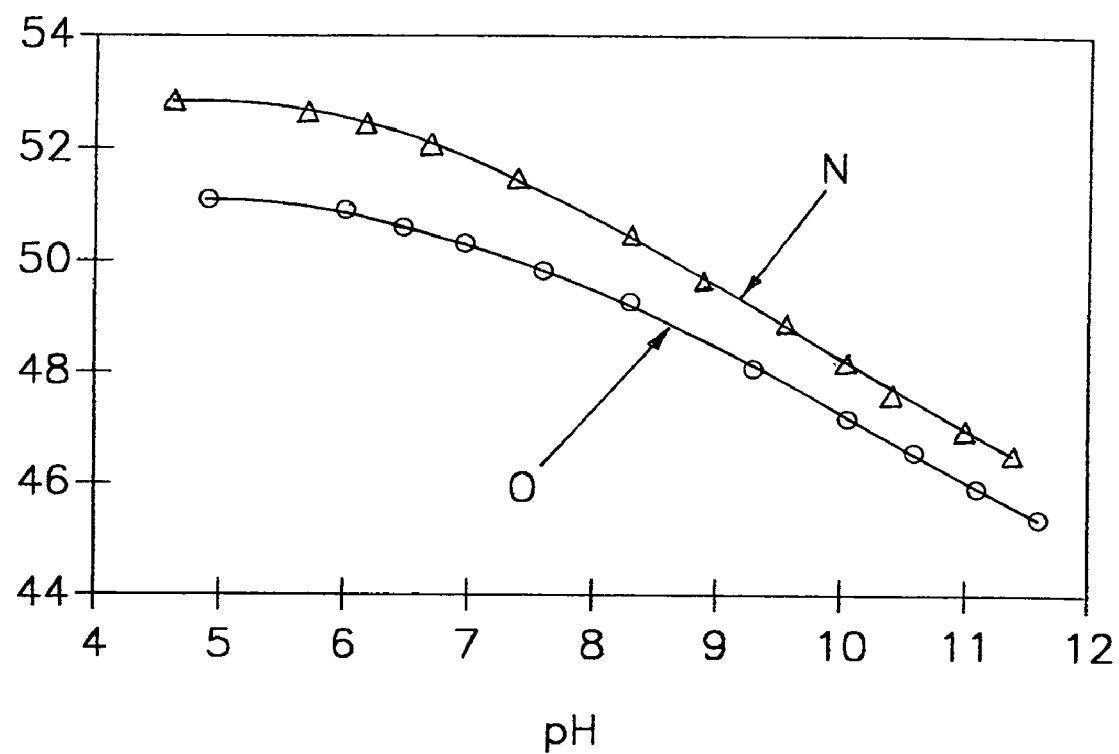
FIG. 1 displays a calibration curve of a pH reagent.

I) Determination of the pH-Value of a Sample

Optical sensors for pH determination according to the state of the art (cf M. J. P. Leiner and O. S. Wolfbeis "Fiber Optic pH Sensors" in O. S. Wolfbeis "Fiber Optic Chemical Sensors and Biosensors", CRC-Press, Boca Raton, 1991, Vol. 1, Chapter 8) usually contain an absorption dye (chromophore) or fluorescent dye incorporated in an ion-permeable, preferably hydrophilic polymer matrix. In dependence of the pH-value (pH=−log(aH+)) of the sample medium, a thermodynamic equilibrium is established between the protonated and deprotonated forms of the chromophore or fluorophore, respectively. From the concentration ratio of the two forms measurable by optical methods, the pH-value of the sample medium may be obtained.

Reaction:

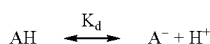

Equilibrium $$K_d = \frac{cA^- * cH^+}{cAH}$$

AH is the protonated, and $A^-$ is the deprotonated form of the pH-sensitive Chromophore. $H^+$ denotes a proton. $K_d$ is the equilibrium constant. c denotes the concentration.

In U.S. Pat. No. 5,232,858 initially mentioned, pH-sensitive chromophores are described, which are attached, preferably covalently, to a pH-insensitive luminophore (donor). From the luminescence decay time of the luminophore (L), the pH-value of the test solution is obtained.

For luminescence-optical pH-determination according to the invention, for example, a pH-sensitive chromophore is used as an acceptor dye, which is provided in the acceptor phase or is at least in direct contact with the acceptor phase, respectively, whereby the acceptor phase may also be the medium to be analyzed (measuring medium).

In the instance of low pH-values (pH<<pK of the chromophore) of the sample medium, the chromophore is present in fully protonated form. Due to the minimal spectral overlap of the absorption band of the deprotonated chromophore and the emission band of the luminophore, the nonradiative energy transfer rate from luminophore to chromophore reaches a minimum. Correspondingly, the values of mean luminescence decay time and relative luminescence intensity of the luminophore reach a maximum.

In the instance of high pH-values (pH>>pKa of the chromophore) of the sample medium, the chromophore is present in fully deprotonated form. Due to the maximal spectral overlap of the absorption band of the deprotonated chromophore and the emission band of the luminophore, the nonradiative energy transfer rate from luminophore (donor, donor dye) to chromophore (acceptor, acceptor dye) reaches a maximum. Correspondingly, the values of mean luminescence decay time and relative luminescence intensity of the luminophore reach a minimum.

For pH-values of the sample medium in the range of +/−1.5 pH units of the pKd value (pKd=−log Kd) of the chromophore, the pH-value of the sample medium may be inferred with sufficient accuracy from the mean luminescence decay time or relative luminescence intensity of the luminophore.

II) Determination of Concentrations and/or Activities of Cations and Anions in a Sample ($Li^+$, $Na^+$, $K^+$, $Mg^{++}$, $Ca^{++}$, C−)

Previously known optical sensors and optical measuring methods, respectively, for determining the concentrations and/or activities of cations in a sample medium are based upon different methods. U.S. Pat. No. 5,232,858 as initially mentioned describes cation-sensitive chromphores which are attached, preferably covalently, to a cation-insensitive luminophore.

In the instance of very high cation concentrations ($cY^{+p}$>>Kd of the chromophore) of the sample medium, the chromophore is present in fully complexed form. (Y is the cation to be determined, +p is its atomic number.) In the instance of very low cation concentrations ($cY^{+p}$<<Kd of the chromophore) of the sample medium, the chromophore is present in free, noncomplexed form.

If the logarithmic concentration $\log(cY^{+p})$ of the cation to be determined of the sample medium is in the range of −log(Kd)+/−1.5, the concentration of the cation to be determined in the sample medium may be inferred with sufficient accuracy from the mean luminescence decay time and/or relative luminescence intensity of the luminophore.

Further optical measuring methods and sensors, respectively, for determining the concentrations and/or activities of cations are known, for example, from U.S. Pat. No. 4,645,744, EP-A-0 358 991 and EP-A-0 461 392, where a pH-sensitive chromophore or a pH-sensitive luminophore, respectively, and a neutral ionophore are provided in a substantially hydrophobic polymer matrix. The disclosed measuring method is based on that cations ($Y^{+p}$) are exchanged with the sample medium (for example, $K^+$ for $H^+$ or $Ca^{++}$ for $2H^+$). As a consequence, the measured results are dependent on the pH-value of the sample medium. Such measuring methods are suitable under measuring conditions in which the pH-value of the sample medium is known or may be adjusted to a known value by means of a pH buffering layer.

In further development according to the invention of these methods, a pH-sensitive chromophore located in the acceptor phase or at least contacting the same and a pH-insensitive luminophore located in the donor phase as well as a neutral ionophore (I) selective for the cation to be determined and located in the acceptor phase are provided for determination of the cationic concentration.

From EP-A-0 358 991 and Anal. Chim. Acta 255 (1991), p. 35–44, optical sensors for determining anions, for example Cl⁻, are known, whereby the anion to be determined is co-extracted from the measuring medium together with a cation (for example, Cl⁻ and H⁺). In that instance, a lipophilic, pH-sensitive chromophore (fluorescein derivative) and an optically inactive, cationic substance ($Q^+$) are provided in a substantially hydrophobic polymer matrix.

In dependence of the $H^+$ and $Cl^-$ concentrations of the measuring medium, the pH-sensitive chromophore located in the polymer matrix is present in protonated and/or deprotonated form. Absorption of the deprotonated form will rise with a growing degree of deprotonation. The degree of deprotonation (and hence, absorption) depends on the pH-value and concentration of the anion to be determined. The pH-value of the measuring medium must be known or adjusted to a known value, so as to indicate the concentration of the anion to be determined.

In further development according to the invention of the disclosed method, for example, a pH-sensitive chromophore located in an essentially hydrophobic acceptor phase permeable to chloride ions of the measuring medium by means of co-extraction or contacting the same (whereby the acceptor phase CANNOT be the measuring medium), a luminophore located in a donor phase as well as a lipophilic, cationic substance (ionophore) are provided for determination of the chloride concentration of a measuring medium. The lipophilic substance (Q+) may be a quaternated ammonium compound, for instance.

Examples of pH-sensitive chromophores used according to the invention are listed below in Table 1. In the instance of low pH-values and high chloride concentrations of the measuring medium, the pH-sensitive chromophore preferably is present in protonated form and the optically inactive, cationic substance forms a counterion to $Cl^-$ in the matrix. Absorption of the deprotonated form of the chromophore reaches a minimum. The values of mean luminescence decay time and relative luminescence intensity of the luminophore reach a maximum.

In the instance of high pH-values and low chloride concentrations of the measuring medium, the pH-sensitive chromophore preferably is present in deprotonated form, the optically inactive, cationic substance compensating the negative charge generated by dissociation of the proton. Absorption of the deprotonated form of the chromophore reaches a maximum. The values of mean luminescence decay time and relative luminescence intensity of the luminophore reach a minimum.

If the pH-value of the measuring medium is known, the chloride concentration of the measuring medium may be inferred from the values of mean luminescence decay time and/or relative luminescence intensity of the luminophore.

III) Determination of Components of Liquid or Gaseous Measuring Media, which Exhibit Weak Acid or Basic Reactions in Aqueous Environments and are Gaseous Under Normal Conditions:

Determination of $CO_2$

Optical sensors for determination of the $CO_2$ partial pressure of a liquid or gaseous measuring medium usually comprise a reaction space which is separated from the medium being measured by an ion-impermeable, gas-permeable material. The reaction space is often identical with the indicator substrate material of an optical pH sensor. In addition, the reaction space usually includes one or several pH buffering substances, such as carbonates, phosphates, and/or organic compounds exhibiting acid or basic reactions in aqueous media. As a consequence, the $pCO_2$ determination of the measuring medium may be traced back to optical pH determination.

In a variant of this measuring principle described in EP-A-0 105 870, the reaction space is provided in the shape of "droplets" in an ion-impermeable, gas-permeable polymer material. In a variant of this measuring principle described in U.S. Pat. No. 5,496,521, the reaction space is provided in the shape of a hydrophilic layer covered by an ion-impermeable, gas-permeable polymer material.

Reaction:

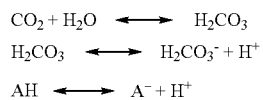

AH is the protonated, and $A^-$ is the deprotonated form of the chromophore. $H^+$ denotes a proton.

In further development according to the invention of the luminescence-optical $CO_2$ determination, a donor shielded from chemical parameters according to the invention and a pH-sensitive acceptor dye are provided in a hydrophilic reaction space separated from the measuring medium by an ion-impermeable, gas-permeable material.

$CO_2$ determination by means of the sensors according to the invention comprising a reaction space containing an aqueous pH buffer and an ion-impermeable, gas-permeable material separating the reaction space from the measuring medium is traced back to the determination of the pH-value in the reaction space of the sensor. High $CO_2$ values of the measuring medium correspond to low pH-values of the reaction space, and low $CO_2$ values of the measuring medium correspond to high pH-values of the reaction space.

An alternative method of optical $CO_2$ determination, for which only a single reaction space without the aid of aqueous pH buffering substances is required, is described by Mills et al. in Anal. Chem. 64, 1992, 1383–1389. In that case, the deprotonated form of a pH-sensitive chromophore with an optically inactive, cationic substance ($Q^+$) is present in a reaction space consisting of an essentially ion-impermeable, gas-permeable polymer material. $CO_2$ of the measuring medium diffusing into the polymer material is hydrated and reacts in a chemcial equilibrium reaction with the deprotonated form of the chromophore and the optically inactive substance. From the light absorption of the deprotonated form of the chromophore, the $CO_2$ partial pressure of the measuring medium is inferred.

Reaction:

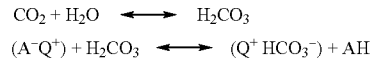

In a variant according to the invention of the luminescence-optical $CO_2$ determination, an essentially lipophilic, pH-sensitive chromophore located in an acceptor phase essentially impermeable to ionic substances in the instance of aqueous measuring media or at least contacting the same, a luminophore located in a donor phase as well as an essentially lipophilic, cationic substance located in the acceptor phase are provided.

Reaction:

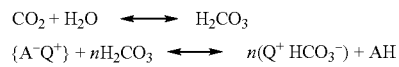

$CO_2 + H_2O \rightleftharpoons H_2CO_3$ $\{A^-Q^+\} + nH_2CO_3 \rightleftharpoons n(Q^+ HCO_3^-) + AH$ According to the invention, $CO_2$ determination by means of a sensor comprising a reaction space without aqueous buffering substances is traced back to the determination of the ratio of the protonated and deprotonated forms of a pH-sensitive chromophore.

In the instance of very low $CO_2$ values of the measuring medium, the chromophore preferably is present in deprotonated form and forms a ionic bond with the optically inactive, cationic substance in the matrix. Absorption of the deprotonated form of the chromophore reaches a maximum. The values of mean luminescence decay time and relative luminescence intensity of the luminophore reach a minimum.

In the instance of high $CO_2$ values of the measuring medium, the chromophore is present in protonated form. The optically inactive, cationic substance forms a ionic bond with hydrogen carbonate. Absorption of the deprotonated form of the chromophore reaches a minimum. The values of mean luminescence decay time and relative luminescence intensity of the luminophore reach a maximum.

Determination of $NH_3$

The determination of $NH_3$, as an example of a component exhibiting a basic reaction in aqueous environment, may be effected in a way similar to the determination of $CO_2$ according to Mills. (T. Werner et al., Analyst 120, 1995, 1627–1631). No optically inactive, cationic substance is necessary.

Reaction:

$AH + NH_3 \rightleftharpoons (A^-NH_4^+)$

The determination of $NH_3$ according to the invention is done by analogy with the CO2 determination according to the invention:

pH-sensitive chromophores suitable for use according to the invention:

TABLE 1

| pH-sensitive chromophores | | |
|---|---|---|
| Chromophore | Absorption wavelength [nm] protonated/deprotonated | pKa |
| Triphenylmethane dyes: | | |
| Bromophenol blue | 430/617 | 3.8 |
| Bromothymol blue | 430–435/615–618 | 6.7 |
| Dibromoxylenol blue | 420/614 | 7.6 |

TABLE 1-continued

| pH-sensitive chromophores | | |
|---|---|---|
| Chromophore | Absorption wavelength [nm] protonated/deprotonated | pKa |
| Azo dyes: | | |
| Calmagit | 530/605 | 8.0 |
| Nitrazine yellow | 460/590 | 6.5 |
| Others: | | |
| o-chlorophenol-indophenol | 555/625 | 7.1 |
| Naphthol-phthalein | 428/661 | 6.7, 7.9 |

In addition, pH-sensitive triphenylmethane dyes of the general form

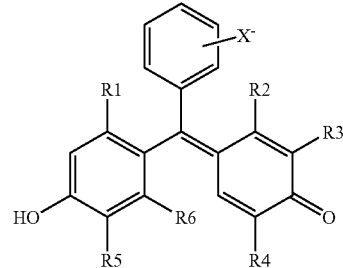

are used. Independently of each other, R1–6 may be H, halogen atoms, nitro groups and alkyl groups. X⁻ stands for an optional group for covalently immobilizing the chromophore. Suitable groups are, for example —(CH?)ₙ—SO3⁻ or —(CH₂)ₙ—COO⁻, —(CH₂)ₙ—NH₂ (n=0–18).

pH-sensitive azo dyes of the general form

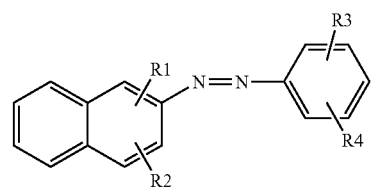

wherein, independently of each other, R1–R4 stand for substituents, such as halogen atoms, nitro groups or alkyl groups, respectively, and groups suitable for covalent immobilization, whereby, however, at least one —OH group has to be present.

Cation-sensitive chromophores (chromoionophores) suitable for use according to the invention:

Examples of cation-sensitive chromoionophores usable according to the invention for determination of lithium, potassium, sodium, magnesium and calcium ions include anionic azo dyes, stilbene dyes and merocyanines, which contain at least one ion-selective group (ionophore group) and whose absorption band with the longest wavelengths overlaps the emission band of the luminophore at least partially, the interaction with the cations to be determined leading to a spectral shift of the absorption band with the longest wavelengths.

Neutral ionophores are listed below in Table 2.

TABLE 2

Neutral ionophores (suitable for ion exchange) Sensors

| Ionophor | Ion |
| --- | --- |
| PTM14C4 (14-crown-4)** | Li+ |
| Sodium Ionophore I-II* | Na+ |
| Valinomycin | K+ |
| Magnesium Ionophore ETH 3832* | Mg++ |
| Calcium Ionophore I-IV* | Ca++ |

*Ionophores for Ion-Selective Electrodes and Optodes. Fluka Chemie AG, CH-9470 Buchs, Switzerland.
**K. Wanabe et al. Anal.Chem. 65, 1993.

TABLE 3

Luminophore (donor dyes)

| Luminophore (L) | Abbrev. | Absorption maximum (nm) | Luminescence maximum (nm) |
| --- | --- | --- | --- |
| (Ru(II)-tris-2,2'-bipyridyl)$^{2+}$ | Ru(bpy)$_3^{2+}$ | 452 | 628 |
| (Ru(II)-tris-2,2' 4,4-diphenyl bipyridyl)$^{2+}$ | Ru(dph-bpy)$_3^{2+}$ | 474 | 632 |
| (Ru(II)-tris-1,10-phenanthroline)$^{2+}$ | Ru(phen)$_3^{2+}$ | 447 | 604 |
| (Os(II)-bis-terpyridine)$^{2+}$ | | 510 | 729 |
| (Os(II)-tr-1,10-phenanthroline)$^{2+}$ | | 650 | 690 |

Other central atoms used are Ir, Rh, Pd, Pt or Re.

Essentially Hydrophobic, Ion-Impermeable Acceptor Phases:

To produce sensors according to the invention, which exchange the cation to be determined (such as K+) with a proton of the measuring medium or co-extract the anion to be measured (such as Cl—) with a proton of the measuring medium, polymer materials substanially impermeable to ionic substances of the measuring medium are suitable.

These materials are also suitable for preparing sensors according to the invention which are used for determination of gases and/or gaseous components in liquid measuring media.

Preferred are all essentially hydrophobic polymers that are soluble in organic solvents, such as polyvinyl chloride, polystyrenes, polycarbonates, polyethylenes, polyurethanes, silicones, copolymers of polyvinyl alcohol and polyvinyl acetate, and copolymers of polyvinyl chloride, polyvinyl alcohol and/or polyvinyl acetate.

Up to 80% by weight plasticizers may be added to these materials, such as dioctyl sebacate, tris-(2-ethylhexyl)-phosphate, 2-nitrophenyl-octyl-ether, 2-nitrophenyl-butyl-ether.

Essentially hydrophilic, ion-permeable acceptor phases:

To produce sensors according to the invention with pH and ion-sensitive chromophores, hydrophilic, ion-permeable polymers are preferred.

Examples of that are cellulose, polyurethanes with hydrophilic groups, polyhydroxyethylmethacrylates, crosslinked polyvinyl alcohols and/or polyacrylamides.

Materials suitable for donor phases include, for example, hard, unplasticized polymers such as polyacryl nitrile plus derivatives, PVC and polyvinylidene chloride.

Determination of calibration values:

The determination of the calibration curves (FIGS. 1–4) and the O$_2$ dependencies was carried out by determining the phase shift of the luminescence with regard to the excitation light modulated in sinusoidal fashion. Due to the use of a long-lived luminophore, a simple measuring arrangement exhibiting a modulation frequency of 45 kHz is sufficient.

For the purpose of measuring, sensor disks were punched from the sensor foils, they were attached to the end piece of a two-armed light guide bundle and were contacted with the respective measuring media, or the end piece of the light guide bundle was dipped directly into the measuring medium containing the sample. A blue LED (470 nm) supplied with an amplitude voltage of 5V, which had been modulated up to 45 kHz in sinusoidal fashion, was used as an excitation light source. Blue foil filters were used as filters for the excitation light. The excitation light was guided to the sensor foil or to the test liquid, respectively, by means of light guides. The emitted luminescence light was guided to a filter, a combination of a OG 570 glass filter (Schott) and a red foil filter, by means of a light guide bundle and was further guided onto a detector (photo multiplier, type Hamamatsu H5702). The distribution voltage modulated in sinusoidal fashion of the LED and the signal of the detector were evaluated by means of a lock-in amplifier. The phase shift $\phi$ was obtained as a measuring signal. The decay time $\tau$ was calculated from the measured phase shift $\phi$ and the modulation frequency f=45 kHz according to the following formula: $\tau=\tan(\phi)/(2\pi f)$.

Phosphate buffers which had been adjusted to the desired pH-values with the aid of NaOH or HCl, respectively, were used as measuring and/or calibration media for the pH sample (FIG. 1) or the pH sensors (FIG. 2), respectively. The buffers were adjusted to the atmospheric oxygen value by employing tonometrics with air or were rendered oxygen-free by adding Na$_2$SO$_3$. Mixed gases of various compositions of N$_2$, O$_2$ and CO$_2$ were used as calibration media for CO$_2$ sensors (FIGS. 3 and 4).

FIG. 1 shows the calibration curve of an optical pH reagent based upon the FRET-principle (produced in accordance with 2.3) and containing a pH-sensitive acceptor dye, the donor dye being present "in protected fashion" in a donor phase of the invention. The two curves show the phase angle (ordinate) of the luminescence light of the pH sample dispersed in calibration liquids exhibiting differing pH-values (abscisse). The curve denoted by "O" was taken up when being saturated by air (21.95% O$_2$). The curve denoted by "N" was taken up when being saturated by N$_2$.

Figure 2:
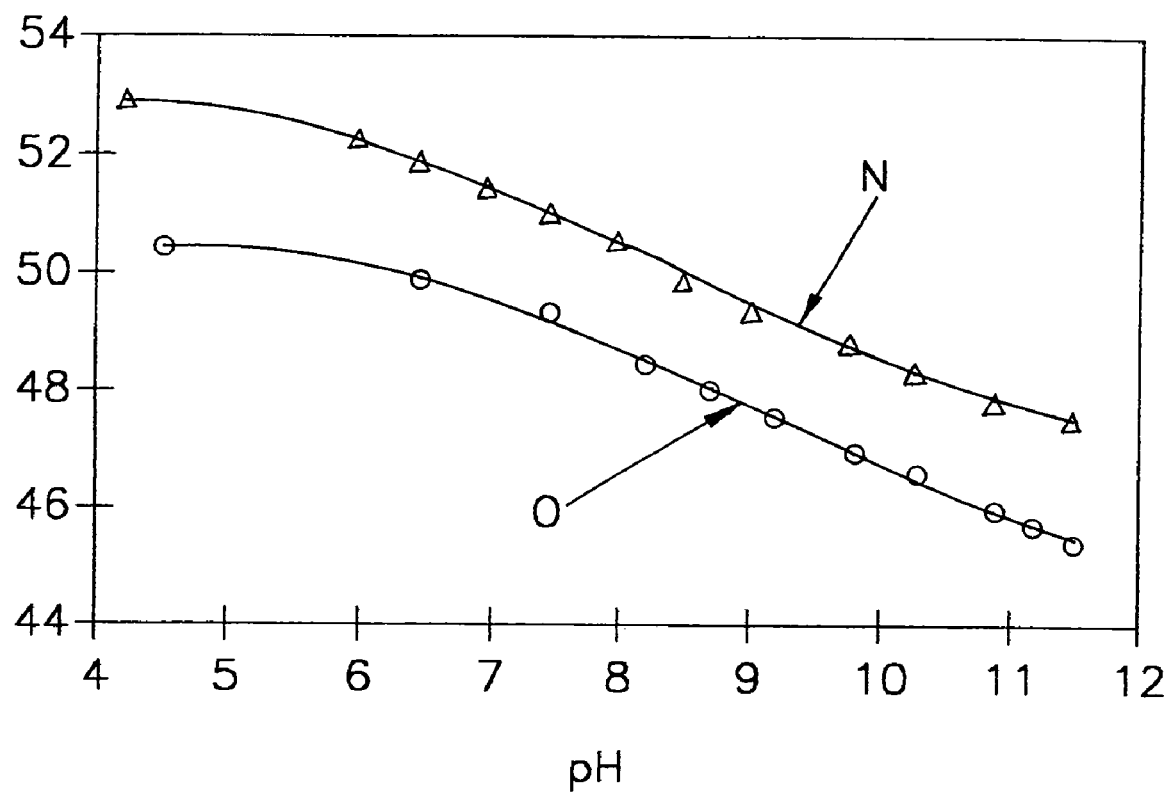
FIG. 2 displays a calibration curve of a pH sensor according to the invention.

FIG. 2 shows the calibration curve of an optical pH sensor based upon the FRET-principle (produced in accordance with 2.4), the donor dye being present "in protected fashion" in a donor phase of the invention. The two curves "N" and "O" refer to the same samples as explained for FIG. 1 and depict the phase angle (ordinate) with calibration liquids exhibiting differing pH-values (abscisse).

Figure 3:
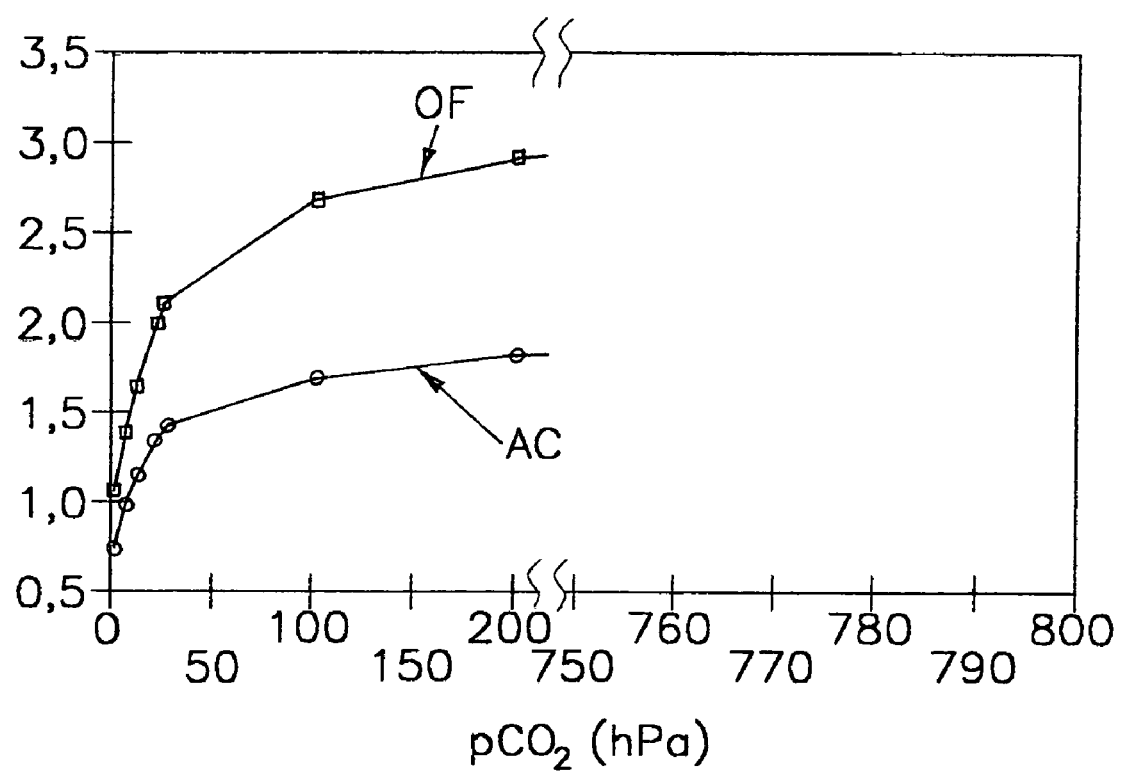
FIG. 3 displays a calibration curve of a $CO_2$ sensor according to the state of the art.
Figure 4:
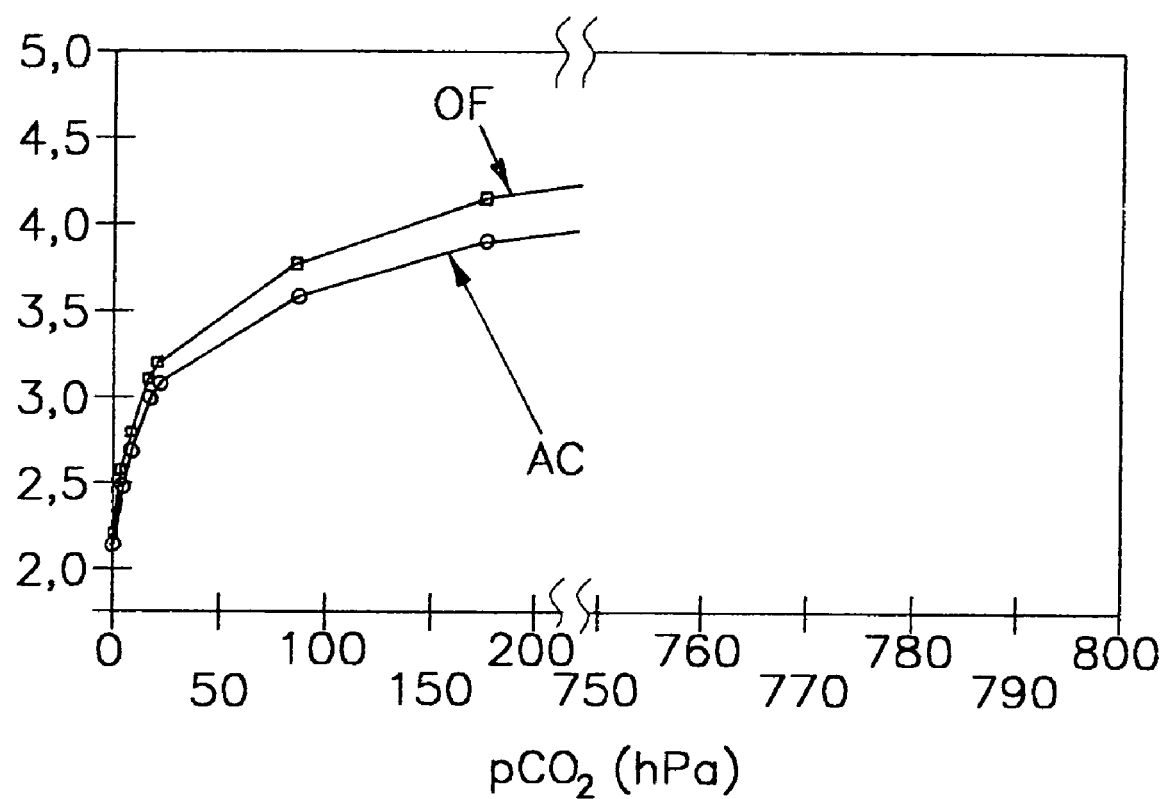
FIG. 4 displays a calibration curve of a $CO_2$ sensor according to the invention.

FIG. 3 shows the calibration curve of an optical CO$_2$ sensor based upon the FRET-principle (produced in accordance with 3.1), the donor dye being present "in unprotected fashion" in the acceptor phase. The two curves depict the luminescence decay times (ordinate) with calibration gases of differing partial pressures of CO$_2$ (abscisse). The curve "OF" means oxygen-free. The curve "AC" means "state of the air" with 21.95% O$_2$.

FIG. 4 shows the calibration curve of an optical CO$_2$ sensor based upon the FRET-principle (produced in accordance with 3.2), the donor dye being present "in protected fashion" in a donor phase of the invention. The two curves (meanings of "OF" and "AC" as in FIG. 3) depict the luminescence decay times (ordinate) with calibration gases of differing partial pressures of CO$_2$ (abscisse).

Figure 5:
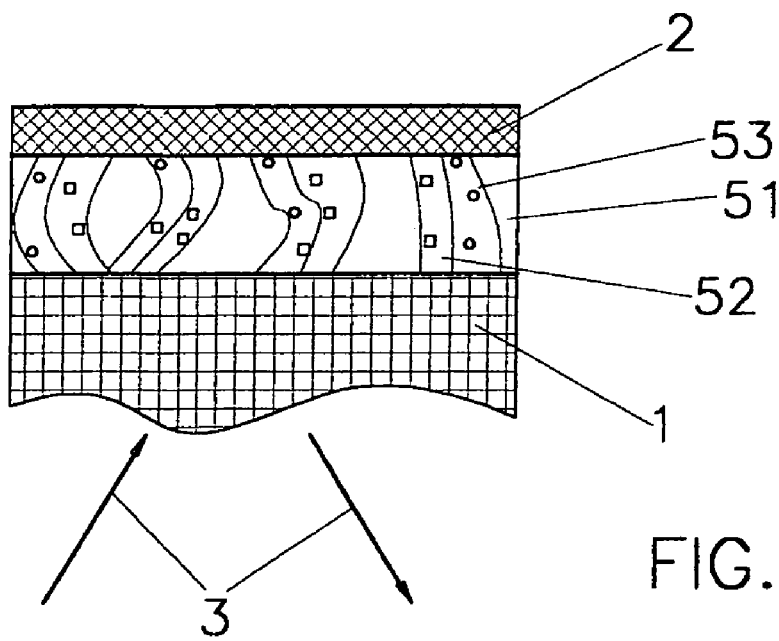
FIG. 5 shows an embodiment of a sensor according to the invention in schematic representation.

FIG. 5 shows a preferred embodiment of the sensor according to the invention. Therein, 1 means optically transparent carrier
2 means optical insulation layer (optional)
3 means light descending on the sensor or emerging therefrom
51 means porous material
52 means donor phase with donor dye (small squares)
53 means acceptor phase with acceptor dye (small circles)

Figure 6:
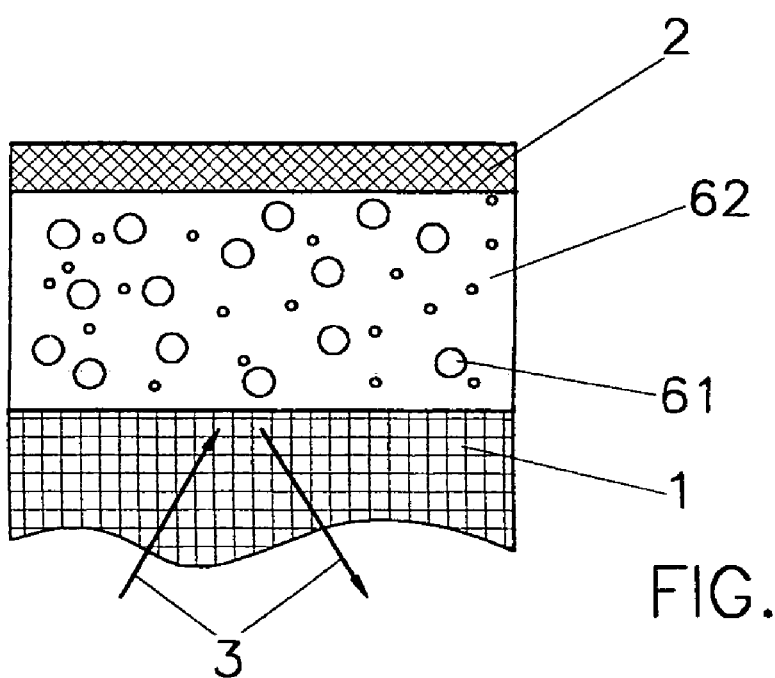
FIG. 6 shows an embodiment of a sensor according to the invention in schematic representation.

FIG. 6 shows a further preferred embodiment of the sensor according to the invention, with reference numerals 1, 2 and 3 having the same meanings as in FIG. 5. Futhermore, 61 means donor phase with donor dye (larger circles)
62 means acceptor phase with acceptor dye (smaller circles)

Figure 7:
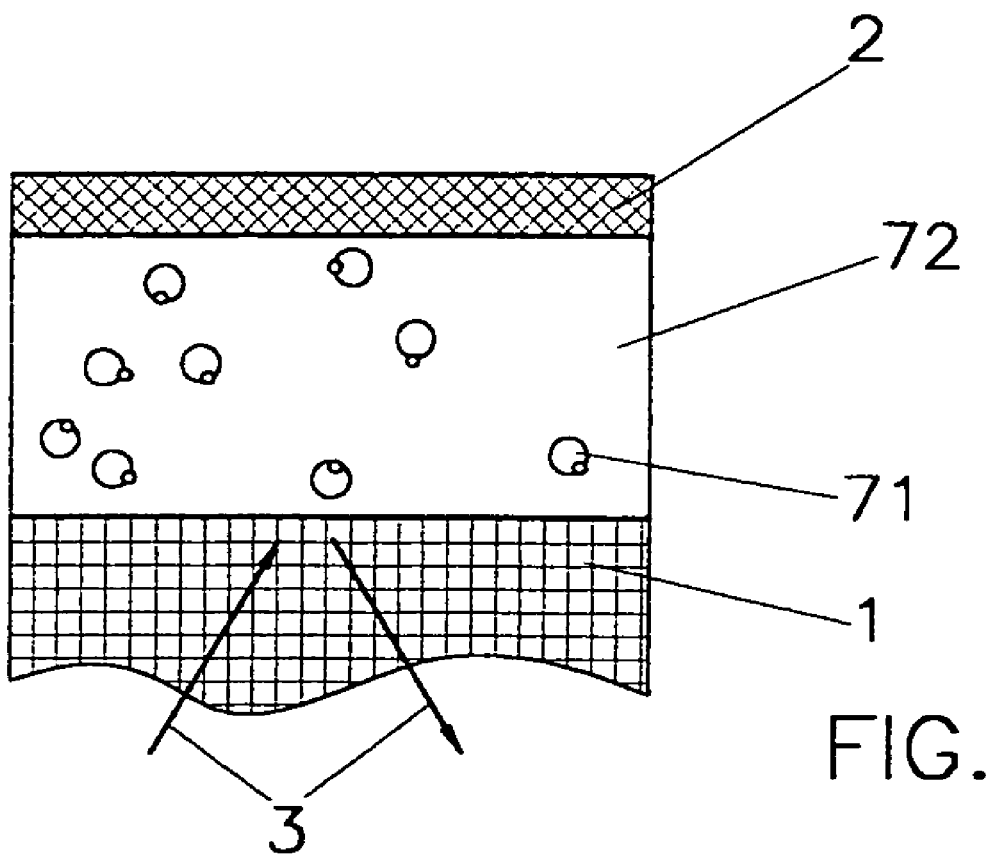
FIG. 7 shows an embodiment of a sensor according to the invention in schematic representation.

FIG. 7 shows a further preferred embodiment of the sensor according to the invention, with reference numerals 1, 2 and 3 having the same meanings as in FIG. 5. Futhermore, 71 means donor phase with donor dye (larger circles) and with bound acceptor dye (smaller circles)
72 means acceptor phase

EXAMPLES

Ru(diphphen)$_3$TMS$_2$ [Ru(II)-tris-(4,7-diphenyl-1,10-phenanthroline)(3-trimethylsilyl)-1-propane sulphonate] (I. Klimant and O. S. Wolfbeis, Anal. Chem. 67 (1995) 3160).

Example 1

This example shows that a donor dye which, according to the invention, is embedded in a donor phase exhibits less $O_2$ sensitivity than the same dye being embedded in the acceptor phase.

General description of the preparation of nanoparticles with embedded donor dye 1.1 Embedding of a Donor Dye into an Acceptor Phase mg donor dye Ru(diphphen)$_3$TMS$_2$ and 100 mg of the hydrophilic polymer D4 (polyurethane with hydrophilic sequences; Tyndale Plains Hunter LTD, Ringoes, N.J. 08551, USA) were dissolved in ethanol:water (90:10 w/w). The solution was drawn up a polyester foil (Mylar, Dupont) by knife application. After evaporation of the solvent, a film with a layer thickness of approximately 20 μm emerged.

| Measuring arrangement (45 kHz, blue LED, OG 570) | | | | |
|---|---|---|---|---|
| Dry: | air | 55.4° | N2: | 58.3° |
| Water: | Air saturated: | 53.5° | N2 saturated: | 58.4° |

The measuring result shows that the donor dye Ru(diphphen)$_3$ $_{TMS2}$ being present "in unprotected fashion" in an acceptor phase exhibits an $O_2$ sensitivity of 2.9° (dry acceptor phase) or of 4.9° (wet acceptor phase), respectively, when getting into contact with $O_2$-free (N2 saturation) or 21.95% $O_2$ (air) saturated, gaseous and aqueous media.

1.2 Preparation of Nanoparticles with Donor Dye 400 mg polyacryl nitrile (Polyscience) and 8 mg Ru(diphphen)$_3$TMS$_2$ were dissolved in 80 ml DMF (Merck). After slowly dripping in 500 ml of water, the emerged suspension was mixed with NaCl and was centrifuged. The centrifuge effluent was washed with water several times and subsequently with ethanol.

1.3 Embedding of the Donor Dye Carrying Nanoparticles into a Stratified Acceptor Phase The ethanolic suspension (of 1.2) was mixed with a solution of 400 mg hydrophilic polymer D4 (Tyndale Plains Hunter LTD, Ringoes, N.J. 08551, USA) in 5 ml ethanol:water (90:10 w/w). The suspension was drawn up a polyester foil (Mylar, Dupont) by knife application. After evaporation of the solvent, a film with a layer thickness of approximately 20 μm emerged.

| Measuring arrangement (45 kHz, blue LED, OG 570) | | | | |
|---|---|---|---|---|
| Dry: | air | 57.4°; | N2: | 58.2° |
| Water: | Air saturated: | 56.8° | O2 free (SO$_3^{2-}$): | 58.6° |

The measuring result shows that the donor dye Ru(diphphen)$_3$ $_{TMS2}$ embedded in a nanoparticle of the invention and thus being present "in protected fashion" in the donor phase exhibits an $O_2$ sensitivity of 0.8° (dry acceptor phase) or of 1.60 (wet acceptor phase), respectively, when getting into contact with $O_2$-free or 21.95% $O_2$ saturated, gaseous or aqueous media.

By comparing these values with the values of 1.1, it thus becomes apparent that one and the same donor dye which is present in a donor phase according to the invention exhibits less $O_2$ sensitivity than the donor dye which, according to the state of the art, is present directly in the acceptor phase.

Example 2 (pH Sensor)

General Description of the Preparation of pH Functional Nanoparticles and a pH-Sensitive Layer In a first step, a OH functional copolymer made up of acrylonitrile and an OH functional methacrylate is prepared. In a second step, nanoparticles containing embedded donor dye are produced from that polymer. In a third step, a pH-sensitive acceptor dye is covalently attached to the functional groups of the copolymer. In doing so, the acceptor dye is located predominantly in the "soft" hydrophilic regions (acceptor phase) of the particles, thus being accesible for ions. The donor dye is dissolved predominantly in the "hard" regions (donor phase), thus making it difficult for interfering substances to gain access. In a fourth step, the particles are suspended in a solution of a hydrophilic polymer, and the solution is deposited on a suitable carrier material. After evaporation of the solvent, a pH-sensitive sensor film emerges.

2.1 Preparation of the Copolymer 230 g de-ionized H$_2$O were rendered oxygen-free by 2 h of rinsing with nitrogen. Under stirring and a nitrogen environment, 4 g SDS (sodium dodecyl sulphate p.A., Merck) were dissolved. 20 ml acrylonitrile (Fluka) and 1 ml polyethylene glycolmonometacrylate (Polyscience, n=200, order no. 16712) were added to that solution. That mixture was taken to 50° and mixed with 4 ml 1 N HCl (Merck). Polymerization was started by adding 400 mg ammonium peroxodisulphate (Merck) and was carried out for 12 h at 50°. The polymer was sucked off and washed several times with water and ethanol. In the following, this polymer is called PAN-PEG.

2.2 Preparation of Nanoparticles with Donor Dye 400 mg PAN-PEG and 20 mg of the donor dye Ru(diphphen)$_3$TMS$_2$ were dissolved in 80 ml DMF (Merck). After slowly dripping in 500 ml of water, the suspension was mixed with NaCl and was centrifuged. The centrifuge effluent was washed with water several times.

2.3 Binding of the pH-Sensitive Acceptor Dye of the Chromophore to the Nanoparticles 25 mg of the pH-sensitive acceptor dye N9 (Merck) were pulverized with 8 Tr. $H_2SO_4$ conc. (Merck) and were activated for 30 min in a water jet vacuum. The dye was absorbed in 100 ml de-ionized water and was taken to pH 7 with the aid of NaOH. The above described centrifuge effluent was added to this mixture, after 5 min 4.2 g $NaCO_3$, and after 5 min 2 ml 5 M NaOH were added. After further 20 min, acidification to pH 3 by means of HCL conc. was carried out. The particles were split off by centrifugation and were washed with basic buffer, water and ethanol.

The thus produced particles were suspensed into an aqueous measuring medium, and the measurements were carried out at various pH-values and unter air and N2 saturation. The result is depicted in FIG. 1 and shows that, for the purpose of pH determination, the pH-sensitive particles may be added to the measuring medium also as reagents (="probe").

Measuring medium: pH 7.3 Air saturated: 50.0° $O_2$-free (N2 saturated): 51.3°

2.4 Preparation of the pH-Sensitive Layer (with Particles of 1.3) of an Optical pH Sensor The ethanolic suspension (2.3) was mixed with a solution of 400 mg hydrophilic polymer D4 (Tyndale Plains Hunter LTD, Ringoes, N.J. 08551, USA) in 8 ml 90% (w/w) ethanol. The suspension was drawn up a polyester foil (Mylar, Dupont) by knife application. After evaporation of the solvent, a pH-sensitive film with a layer thickness of approximately 20 μm emerged.

FIG. 2 shows the pH dependency of the phase signal of the thus produced optical sensor.

pH 7.5 buffer: Air saturated: 49.3° $O_2$-free ($SO_3^{2-}$): 51.3°

Comparing these measuring results with the data of 1.1 shows that an optical pH sensor with a donor dye which is present "in protected fashion" in a donor phase according to the invention exhibits a lower $O_2$ sensitivity (change of the phase angle 2.0° at transition $O_2$-free after air saturation) than the donor dye which is present in the acceptor phase according to the state of the art.

Example 3 ($CO_2$ Sensor)

With that sensor, the luminescent nanoparticles are embedded in a polymer film in which the indirectly $CO_2$ sensitive absorption indicator is present in dissolved form. The difference from the pH sensor (2.4) essentially consists in that, in this case, no covalent coupling of the analyte-sensitive absorption dye to the nanoparticles takes place.

3.1 Embedding of a Donor Dye Used According to the Invention in an Acceptor Phase 5 g ethylcellulose (ethoxyl content 46%, Aldrich, Steinheim, Germany) were dissolved in 100 ml of a toluol:ethanol mixture (20:80, v:v). 100 μL tetraoctyl ammonium hydroxide (611 mmol/kg ethylcellulose) and 1 mg m-cresol purple- (24 mmol/kg ethylcellulose) (m-cresol purple=tridodecyl methylammonium salt, TDMA) were added to 1 g of this solution. 0.7 mg of the donor dye Ru(diph-bpy)$_3$TMS$_2$ (=ruthenium(II)tris-(4,4'diphenyl-2,2'-bipyridyl)(3-trimethylsilyl)-1-propane sulfonate) were added to that solution.

By knife application, the solution was drawn up a polyester foil (Mylar, Goodfellow, UK) with a thickness of 125 μm when exhibiting a wet thickness of 125 μm. After evaporation of the solvent, an approximately 10 μm thick, $CO_2$ sensitive layer was obtained.

3.2 Rules for Manufacturing the $CO_2$ Sensitive Layer of an Optical $CO_2$ Sensor 5 g ethylcellulose (Aldrich) were dissolved in toluol/ethanol (20/80, v/v). 100 μL tetraoctyl ammonium hydroxide (611 mmol/kg ethylcellulose) and 1.08 mg cresol purple-TDMA (24 mmol/kg ethylcellulose) were added to 1 g of this solution.

700 μL (containing 10.1 mg dry weight of particles) of the ethanolic particle suspension (preparation by analogy with 1.2, however, by means of the dye Ru(diph-bpy)$_3$TMS$_2$) were added to that solution. By knife application, the suspension was drawn up a polyester foil (Mylar, Goodfellow, UK) with a thickness of 125 μm when exhibiting a wet thickness of 125 μm. After evaporation of the solvent, an approximately 10 μm thick, $CO_2$ sensitive layer was obtained.

The measuring results are shown in FIGS. 3 and 4 and in Table 4, respectively. The results clearly indicate that a $CO_2$ sensor of the invention based upon the FRET-principle exhibits a significantly lower $O_2$ sensitivity than a sensor produced in accordance with the state of the art.

TABLE 4

Comparison of the two sensors of FIG. 1 (C1) and FIG. 2 (C2). The error indications (two columns on the right) clearly show that, with the sensor according to the invention, the O2 error is significantly smaller.

| | C1 decay time (μs) | | C2 decay time (μs) | | indicated pCO2 error in hPa | |
| --- | --- | --- | --- | --- | --- | --- |
| pCO$_2$ (hPa) | oxygen-free | air saturated | oxygen-free | air saturated | C1 | C2 |
| 0 | 1.05 | 0.74 | 2.19 | 2.14 | +7 | +1 |
| 30 | 2.17 | 1.44 | 3.29 | 3.12 | >800 | +12 |
| 60 | 2.41 | 1.56 | 3.52 | 3.36 | >800 | +15 |
| 100 | 2.71 | 1.70 | 3.81 | 3.61 | >800 | +46 |

Example 4 ($CO_2$ Sensor)

This sensor consists of a nanoporous membrane (Teflon membrane of Millipore) coated with a thin film of polyacryl nitrile into which the donor dye is embedded. This is done by simple soaking of the porous membrane with the donor cocktail and subsequent evaporation of the solvent. Subsequently, a second coating is prepared by analyte-sensitive colour chemistry (in that case, a $CO_2$ sensor). Thus, donor and acceptor are provided in separate phases.

Manufacturing Rules:

A nanoporous Teflon filter is soaked with a 5% polyacryl nitrile ruthenium complex solution. Subsequently, the solvent is left to evaporate (100° C. for 10 hours). In a second step, the same porous membrane is soaked with the $CO_2$ sensitive cocktail. The cocktail has the following composition:

| | |
| --- | --- |
| Ethylcellulose: | 1 g |
| Ethanol: | 4 ml |
| Toluene: | 16 ml |
| Tetraoctyl ammonium hydroxide: | 250 mg |
| m-cresol purple-TDMA: | 30 mg |

Afterwards, the filter is dried and the sensor is ready for use. 30% decline of the decay time between 100% $CO_2$ and 0% $CO_2$.

The invention claimed is:

1. An optical chemical sensor functioning in accordance with the FRET principle for detecting an analyte in a sample medium comprising:
a donor phase comprising a first luminophore and having an emission spectrum; and
an acceptor phase comprising a chromophore or a second luminophore responsive to the analyte and having an absorption spectrum, wherein
the donor phase is essentially impermeable to the sample medium or components of the medium capable of affecting the luminescence characteristics of the first luminophore,
there is at least partial overlap between the emission spectrum of the donor phase and the absorption spectrum of the acceptor phase, and
the acceptor phase is in sufficient spatial proximity to the donor phase for nonradiative energy transfer.

2. The sensor of claim 1 wherein the donor phase comprises a donor matrix material and the acceptor phase comprises an acceptor matrix material.

3. The sensor of claim 2 further comprising a mixture of the donor matrix material and the acceptor matrix material.

4. The sensor of claim 3 wherein the donor matrix material is homogenously distributed in the acceptor matrix material.

5. The sensor of claim 4 wherein the donor matrix material comprises particles having the first luminophore embedded therein.

6. The sensor of claim 3 further comprising a sensor layer comprising a thin layer of the mixture.

7. The sensor of claim 6 wherein the sensor layer is attached to a transparent substrate.

8. The sensor of claim 6 wherein the sensor layer is attached to a light guide.

9. The sensor of claim 6 further comprising an optical insulation layer permeable to the analyte and located between the sensor layer and the sample medium.

10. The sensor of claim 2 further comprising a sensor layer comprising a thin porous material wherein the pores of the material contain the donor matrix material and the acceptor matrix material.

11. The sensor of claim 10 wherein the sensor layer is attached to a transparent substrate.

12. The sensor of claim 10 wherein the sensor layer is attached to a light guide.

13. The sensor of claim 10 further comprising an optical insulation layer permeable to the analyte and located between the sensor layer and the sample medium.

14. The sensor of claim 5 wherein the chromophore or second luminophore of the acceptor phase is attached to the surface of the particles.

15. The sensor of claim 1 wherein the donor phase comprises at least one unplasticized polymer.

16. The sensor of claim 15, wherein the at least one polymer comprises at least one of polyacryl nitrile, a derivative of polyacryl nitrile, PVC and polyvinylidene chloride.

17. The sensor of claim 1 wherein the acceptor phase comprises at least one of polyvinyl chloride, polystyrene, polycarbonate, polyethylene, polyurethane, silicone, copolymer of polyvinyl alcohol and polyvinyl acetate, cellulose, polyurethane with hydrophilic groups, polyhydroxyethylmethacrylate, crosslinked polyvinyl alcohol, and polyacrylamide.

18. The sensor of claim 17 wherein the acceptor phase further comprises up to 80% of a plasticizer.

19. A method for the qualitative and/or quantitative determination of an analyte in a sample medium comprising:
providing a sensor according to claim 1; and
contacting the sensor with a sample.

20. The method of claim 19 wherein the pH-value of the sample is determined.

21. The method of claim 19 wherein at least one of the concentration and activity of at least one ion in the sample is determined.

22. The method of claim 19 wherein the analyte is one or more components that exhibits acid or alkaline reactions in aqueous media while being gaseous under normal conditions.

23. The method of claim 21 wherein at least one of the concentration and activity of at least one of $Li^+$, $Na^+$, $K^+$, $Mg^{++}$, $Ca^{++}$, or $Cl^-$ is determined.

24. The method of claim 21 wherein $CO_2$ or $NH_3$ is determined in a liquid medium.

25. The method of claim 19 wherein the sample is a body fluid.

26. The method of claim 19 wherein the sample is blood, plasma or serum.

27. The method of claim 19 wherein the sensor is used as a transducer.

28. The method of claim 19 wherein the sensor is an enzymatical sensor.

* * * * *